United States Patent
Vogel

(10) Patent No.: US 10,092,378 B2
(45) Date of Patent: Oct. 9, 2018

(54) METHOD FOR PRODUCING DENTURES AND ARTICULATOR FOR CARRYING OUT THE METHOD

(71) Applicant: AVO SAX-GmbH, Falkenstein (DE)

(72) Inventor: Andreas Vogel, Leipzig (DE)

(73) Assignee: AVO SAX-GmbH, Falkenstein (DE)

( * ) Notice: Subject to any disclaimer, the term of this patent is extended or adjusted under 35 U.S.C. 154(b) by 507 days.

(21) Appl. No.: 14/398,486

(22) PCT Filed: Apr. 29, 2013

(86) PCT No.: PCT/DE2013/000230
§ 371 (c)(1),
(2) Date: Nov. 3, 2014

(87) PCT Pub. No.: WO2013/163977
PCT Pub. Date: Jul. 11, 2013

(65) Prior Publication Data
US 2015/0111168 A1    Apr. 23, 2015

(30) Foreign Application Priority Data

May 2, 2012 (DE) .................. 10 2012 008 516
Mar. 11, 2013 (DE) .................. 10 2013 004 102

(51) Int. Cl.
*A61C 11/02* (2006.01)
*A61C 13/00* (2006.01)
(Continued)

(52) U.S. Cl.
CPC ............ *A61C 11/02* (2013.01); *A61C 9/0006* (2013.01); *A61C 11/022* (2013.01); *A61C 11/08* (2013.01); *A61C 13/00* (2013.01); *A61C 19/045* (2013.01)

(58) Field of Classification Search
CPC .......... A61C 11/02; A61C 9/006; A61C 11/08; A61C 11/022; A61C 13/00; A61C 19/045
See application file for complete search history.

(56) References Cited

U.S. PATENT DOCUMENTS 3,321,832 A    5/1967  Weisberg
3,965,576 A  * 6/1976  Eveland ............... A61C 11/001
                                                    433/214
(Continued)

FOREIGN PATENT DOCUMENTS

CA          1284041 C      5/1991
DE    102005013459 A1    10/2006
(Continued)

*Primary Examiner* — Nicholas Lucchesi
(74) *Attorney, Agent, or Firm* — James Creighton Wray; Meera P. Narasimhan

(57) ABSTRACT

For producing dentures, a new method and device render it possible to evaluate and shape movements generated by the individual jaw joints of the patient such that work with appropriate articulators becomes possible, which employ the individual jaw joints as articulation joints and thus carry out the identical movements. The known articulators are equipped with joint-space duplicates such that they can be employed with optimal equipment for the respective patient. The support pin is moved back as fixing pin in the retral space of the articulator such that it does not constitute an impediment when working on and when inspecting the jaw models arranged on the frame upper part and the frame base part. Moreover, setting different biting positions is made significantly easier, because the frame upper part is fixed to a swivel arch of the frame base part by an adjustable position stabilizer but can also be detached.

20 Claims, 9 Drawing Sheets

(51) Int. Cl.
*A61C 19/045* (2006.01)
*A61C 9/00* (2006.01)
*A61C 11/08* (2006.01)

(56) References Cited

U.S. PATENT DOCUMENTS

| | | | | |
|---|---|---|---|---|
| 4,886,453 | A | * | 12/1989 | Ludwigs ............ A61C 13/1016 433/54 |
| 5,425,636 | A | * | 6/1995 | Ghim .................... A61C 9/002 433/57 |
| 2004/0131991 | A1 | * | 7/2004 | Sasagawa .............. A61C 11/08 433/60 |
| 2004/0259050 | A1 | * | 12/2004 | Racich ................. A61C 11/001 433/56 |
| 2007/0196782 | A1 | | 8/2007 | Noguchi |
| 2007/0231770 | A1 | * | 10/2007 | Huffman ................ A61C 9/002 433/60 |

FOREIGN PATENT DOCUMENTS

| | | |
|---|---|---|
| EP | 0233857 A1 | 8/1987 |
| WO | 2005060865 A1 | 7/2005 |

* cited by examiner

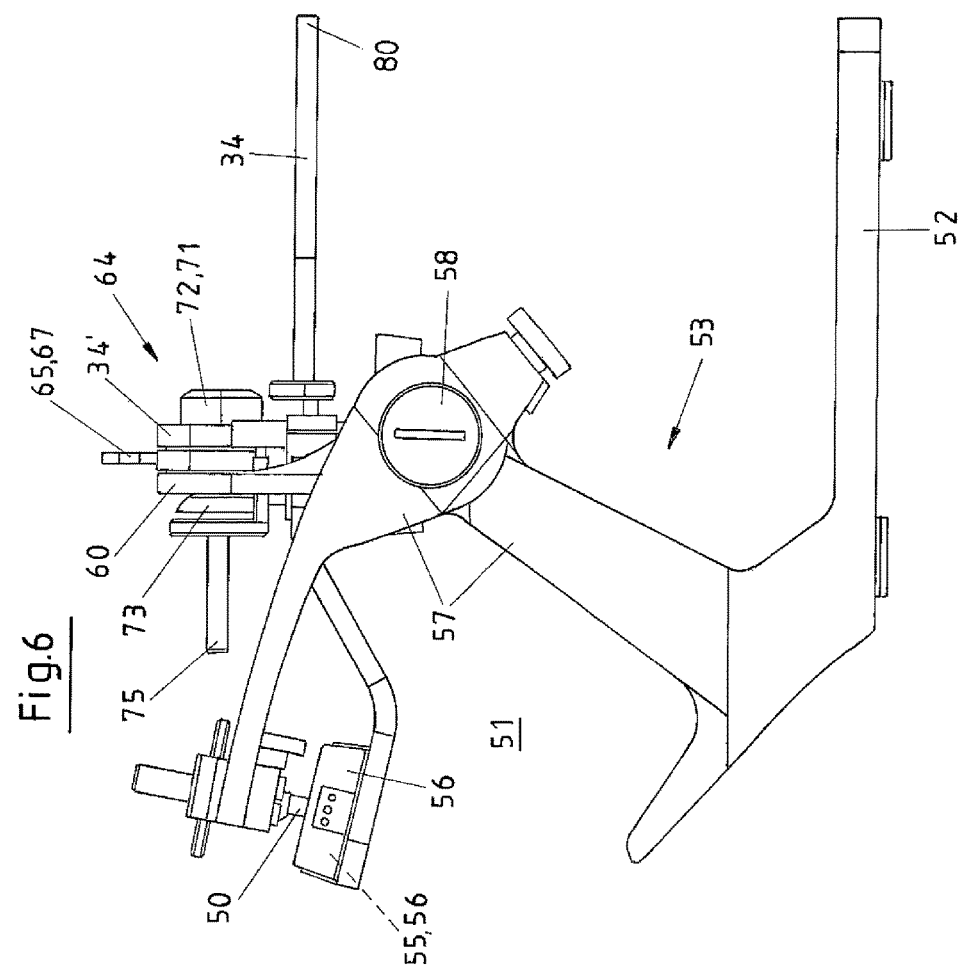

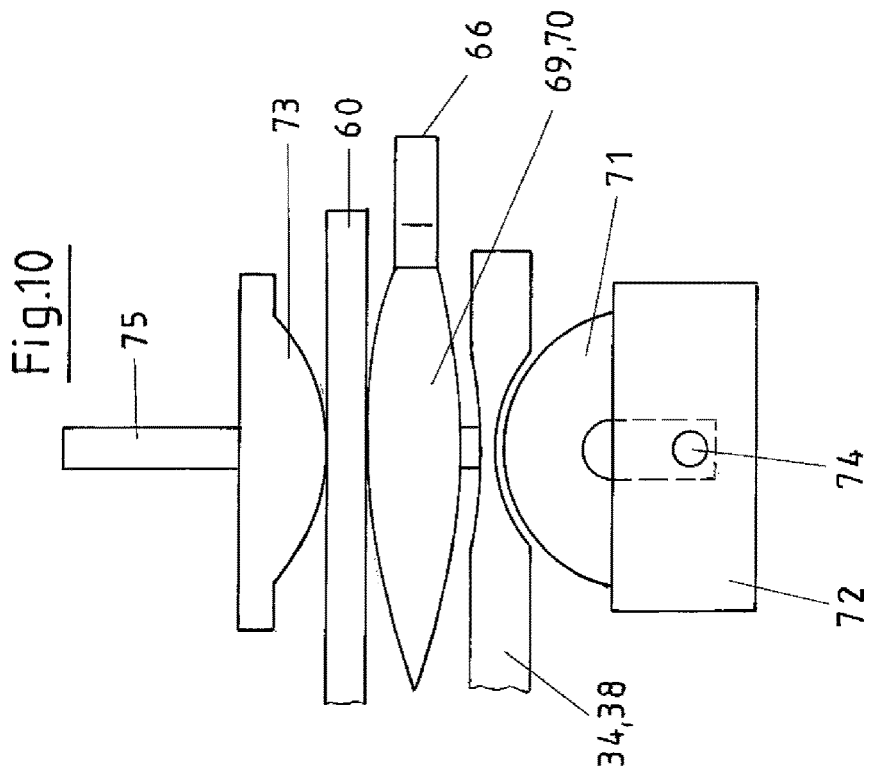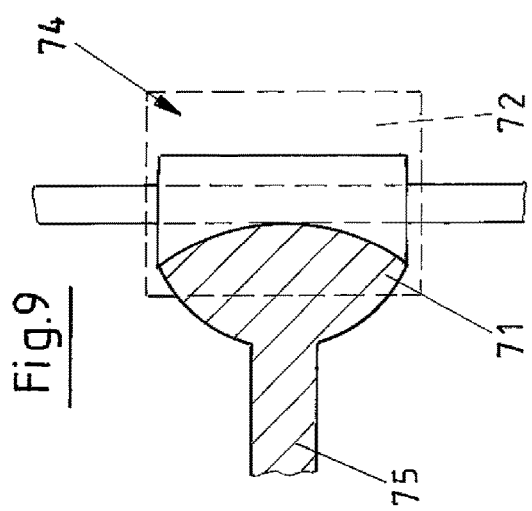

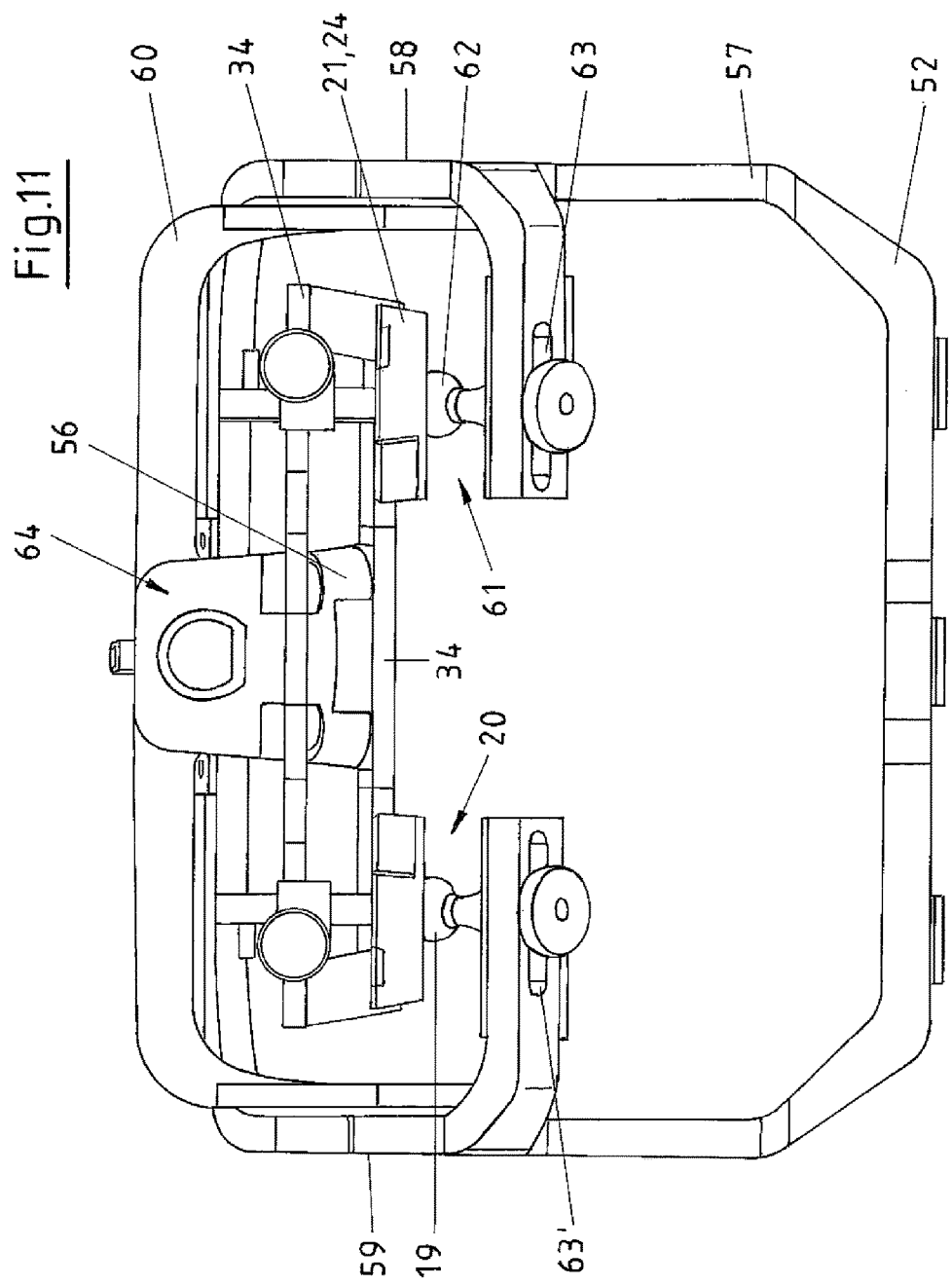

METHOD FOR PRODUCING DENTURES AND ARTICULATOR FOR CARRYING OUT THE METHOD

This application claims the benefit of German Application No. 10 2012 008 516.8 filed May 2, 2012, German Application No. 10 2013 004 102.3 filed Mar. 11, 2013, and PCT/DE2013/000230 filed Apr. 29, 2013, International Publication No. WO 2013/163977, which are hereby incorporated by reference in their entirety as if fully set forth herein.

The invention relates to a method for producing dental prostheses, in which first an impression of the upper jaw and of the lower jaw with the teeth is made, and registration molds receiving the corresponding impressions of the upper and lower jaw in a device called articulator for simulating the movements of the lower jaw are then taken to a dental technician, whereupon the dental prosthesis is molded by moving either the impression of the lower jaw or, in most instances, the impression of the upper jaw around the articulator joints that are similar to the jaw joints of the patient and are produced mostly taking into account the impression of the lower jaw, is then returned to the dentist, inserted in the patient('s mouth), and finished by the dentist. The invention also relates to a device for simulating lower jaw movements and for carrying out the method according to claims 1-8 therewith, consisting of an articulator with an upper jaw model holder with support pin and a lower jaw model holder, wherein the upper jaw model holder and lower jaw model holder are mutually articulately connected via articulator joints, which match the human jaw joints as closely as possible.

Such methods and also articulators are basically known (DE 10 2005 013 459 A1, EP 0 233 857 B1) and are currently used in dental practices and dental technology laboratories. The articulators used for this purpose are very similar in design and are provided with holders for the upper and lower jaw impressions and should then provide the dental technician with the possibility of recreating and reproducing the movements that patients normally perform while chewing. The dental technician can then integrate the replacement teeth into the lower and upper jaw impressions delivered by the dentist and, for example, having gaps, which are then to be connected to the patient's existing teeth. It is important here for the dental technician to be able to recreate the subsequently performed movements with his articulator during the production and testing of the dental prosthesis, or also of complete tooth plates, in such a way that the newly inserted dental structure fits as precisely as possible and does not cause the patient any pain. In doing so, the dental technician or manufacturer of the articulator uses swivel joints for the part of the articulator to be swiveled, which only very generically recreate the natural jaw joints and allow similar movements. Aside from the fact that each person has, as a rule, two differently configured jaw joints on both sides of the head, these jaw joints sometimes differ greatly in several patients. The movements, or movement sequences, carried out with the articulator then no longer correspond to the special patient to be treated in particular, but are normal movements. The consequence is that the dental prosthesis produced and restored in this way does not easily fit in the existing denture. The dentist therefore not only requires, but is even forced to check for himself whether the teeth manufactured in this way meet the requirements in the patient's mouth after inserting the dental prosthesis or the denture. To what extent the dentist must adapt the teeth manufactured by the dental technician so that they then optimally meet the special conditions of use depends on the dexterity of the dentist. The corresponding method for producing the dental prosthesis has been very dependent on many imponderables and skills.

The underlying object of the invention is therefore to create a manufacturing method and a corresponding device, with which restoration work made to measure for the respective patient is possible and easy to perform on the human denture.

As far as the method is concerned, the object is attained according to the invention in that, before or after the impressions of the upper and lower jaw are produced, the movement paths in the basic directions of the patient's jaw joints are determined, registered and used on the articulator for the production (representation) of the joint space duplicates of the patient's jaw joints during the movements of the lower jaw as articulator joints, and that this articulator equipped with articulator joints corresponding to the patient's jaw joints is then used by the dental technician to restore the dental prosthesis.

The registration of the trajectories or corresponding joint space duplicates of the respective special jaw joint is possible by applying the geometric principle of the intercept theorem and its application in the so-called pantograph according to the "three leg principle," wherein the actual and biologically existing individual jaw joint including the patient's disc, can be securely read. It is also possible with the method to manufacture the joint space duplicates corresponding to the actual jaw joints of the respective patient, which will then make it possible for the dental technician, but also for the dentist, to already manufacture teeth during the first step, that is, especially for the dental technician, such that they can be subsequently inserted into the patient ('s mouth) without problems and where finishing can normally be omitted because the exact denture has already been realized in every respect by the dental technician. The effort required to produce the joint space duplicates is not greater than the former finishing at the dentist's, but has the great advantage that all possible positions of the upper and lower jaw with respect to each other, as they will later occur with the corresponding dental prosthesis or the new denture, can be reproduced outside of the patient's mouth. The dental technician manufactures a dental prosthesis by means of the method, which is made exactly to measure for the denture/jaw joints of the respective patient and requires no finishing.

According to a practical embodiment of the invention it is provided that the movements carried out by the patient's lower jaw and the jaw joints guided by means of a support pin, which is fixed via an upper jaw plate in the upper jaw, and hemispheres which are arranged spaced apart from each other via a lower jaw plate, and forming a triangle with the support pin in the axis of the support pin/jaw joint, while decoupling the patient's denture, are transferred as a joint space duplicate to a material embedded in a plastic dental bite registration mold allocated to the upper jaw plate, and that another joint space duplicate of each jaw joint is produced using this joint space duplicate extraorally according to the pantograph principle, and are utilized as articulator joints in the articulator. It is possible in this way to "delineate" the biological jaw joint situation with the help of the patient's chewing force by means of corresponding movements of the lower jaw and constantly maintaining a low chewing force. In this context, the condyles traverse their fossa in constant mechanical contact with each other via the disc. The temporomandibular joint-condyle-fossa correlation is registered with a mechanically reusable and medically flawless bite registration mold, and then again enlarged via the pantograph principle in order to produce the original joint space duplicate, which, when inserted in the articulator, results in a patient's articulator. The jaw joint duplicate is produced extraorally, as a rule probably by a dental technician, wherein the joint space duplicate is normally stored (and) can be used several times for the patient.

With a corresponding adaptation of the respective articulator, it is also possible according to the invention to incorporate the intraoral joint space duplicates directly into the articulator, where they form the articulator joint on interaction with joint balls. This has the advantage that further extraoral joint space duplicates do not have to be manufactured separately via the pantograph principle.

Another practical embodiment of the method provides that the exact occlusion plane is adjusted on the articulator even before or during the manufacture of the dental prosthesis using the Camper's plane measured on the patient when manufacturing the dental prosthesis with the articulator having the joint space duplicates. The so-called occlusal plane requires a specialized dental technology laboratory in order to adjust the correct position between the upper and lower jaw in the articulator. The occlusal plane runs parallel to the Camper's plane, wherein the latter is the imaginary reference line on the skull. It is defined by the anterior nasal spine and the lower boundary of the porus acusticus, that is, it runs approximately between the patient's ear and nose. The latter can also be slightly shortened in the patient, then being adjusted in the articulator to realize the occlusal plane.

Another embodiment of the invention provides that during the manufacture of the corresponding dental prosthesis of any type in an articulator programmed according to the method, the support pin with the upper jaw plate is further fixed in the articulator, while the joint balls and the intraoral joint space duplicates are removed therefrom when the dental prosthesis is manufactured and inspected in the articulator. The support pin and the extraoral joint space duplicates now predetermine the steps for the restoration, whereby the dental technician carries out the necessary model movements. Accordingly, while the support pin is still required for further work, the smaller joint space duplicate can now be removed from the articulator, unless it fits precisely therein.

It has also been pointed out above that the condyles traverse their fossa in constant mechanical contact via the disc during the reproduction of the jaw joint. In order to determine the correct joint space duplicate, it is necessary that the movements of the jaw joints are transformed three-dimensionally in the curable plastic material introduced into the dental bite registration tray resulting in the intraoral joint space duplicates. These three-dimensional movement spaces can then also be exactly transferred and molded to joint space or extraoral duplicates, whereby three-dimensional joint spaces likewise result there.

Consistent with another embodiment of the method according to the invention, the values obtained during the articulation, that is, during the "delineation" of the jaw joint fossa, are additionally or only electronically acquired, stored and used via CadCam or the like to form the joint movement spaces in the dental template/dental bite registration mold, or directly from the joint space duplicates. The use of the above-mentioned geometrical principle for registering the individual jaw joint situation of the patient and their technical implementation is realized regardless of whether it is accomplished with the mechanically produced register or with any other electronic variant, or also other registration methods.

It has also been mentioned above that it is also possible to insert the joint space duplicates or the dental bite registration mold receiving them directly in the articulator and then use them there. In the case of this variant, but also in that of the embodiment of the method explained in detail above, it is advantageous if different dental occlusions are rapidly and securely reproduced, comparatively presented for diagnostic procedures, and, if required, corrected in the occlusion system with the articulator having the joint space duplicates via a correspondingly adjustable position stabilizer during the manufacture of the dental prosthesis and to retain the fixation of the upper jaw model on the upper part of the articulator frame. This embodiment of the method can also be used when working with customary articulators, but the dental occlusion can be varied according to the individual desire of the dental technician or also of the dentist. Until now, it has been necessary to release the respective upper jaw models from the upper jaw model holders and from the upper part of the frame in order to then carry out a corresponding secondary articulation to achieve the respective bite therewith. In doing so, the upper jaw model made from plaster has frequently been destroyed, which causes considerable difficulties and in the end prompts the dental technician to operate the articulator with one predetermined dental occlusion only, which further results in that the dentist must finish the dental prosthesis due to the existing problems. This is precisely not necessary with the described method because, in this case, it is possible to realize corresponding variations of the dental occlusion by means of the adjustable position stabilizer without the need for further adjustments or even changes on the actual articulator.

A device consisting of an articulator and a pre-device is used for the implementation of the method. According to the solution consistent with the device, it is provided that the articulator is configured is a pre-device with a lower jaw plate and support pin, as well as dental bite registration molds, and a lower jaw plate that can be connected to a measuring sensor to be allocated thereto, by means of which joint space duplicates corresponding to the patient's fossa can be molded with the curable plastic material of the dental bite registration mold in the patient's mouth and which are configured and arranged in such a way that the trajectories of the joint space duplicates in the curable joint material can be transferred according to the pantograph principle to the joint registration molds of the articulator joints. The articulator thus receives this pre-device in such a way that the joint space duplicates stored therein can accordingly be realized as enlarged or equal joint space duplicates in order to then serve as correspondingly optimal joint in the articulator joints together with the joint balls. It is possible in this way to equip an articulator of this kind for the first time with articulator joints that exactly match the respective patient's jaw joints and thus may ultimately even be designated as jaw joint duplicates. These joint space duplicates can thus be indeed different on both sides in such an articulator, so that the dental technician is for the first time provided with the possibility to perform the necessary adaptations, tests, et cetera to correctly adapt them to the respective patient, so that the dental prostheses, bridges and the like manufactured therewith can accordingly be manufactured exactly meeting the requirements of the respective patient.

Since the articulator joints or their replacement are to be made to measure for the respective patient, the invention provides that the articulator joints or the joint space duplicates that reproduce the human jaw joint fossa are configured so as to be releasable and replaceable by the joint space duplicates of the respective patient. This means that the articulator is delivered by the actual manufacturer with standard articulator joints, which are, however, releasably connected to the actual articulator in comparison with the swivel joints used until now. These articulator joints can thus be replaced by means of an articulator joint made to measure for the respective patient, which then makes possible the correct processing or restoration.

It is furthermore practical if the pre-device has a releasable upper jaw plate with support pin and a releasable lower jaw plate with transfer pins configured as hemispheres as measuring sensors, which are arranged therewith forming a triangle in the support pin/jaw joint axis, if the upper jaw plate is equipped, besides the support pin, with dental bite registration molds filled with plastic curable material, which are positioned in correspondence with the hemispheres of the measuring sensor, and if the articulator joints of the articulator are formed by the joint space duplicates of the respective patient with the joint balls of the articulator joint, which are produced extraorally corresponding to the jaw joints of the patient by scanning the movement space/fossa in the dental bite registration mold according to the pantograph principle into the plastic curable joint material in the joint registration mold, and which are arranged at the swivel joint site of the articulator. The necessary tripod consisting of the support pin and the transfer pins is represented here by hemispheres and the identical support pin, wherein the correspondingly reduced "jaw joint" is reproduced in the plastic curable material. This is carried out mechanically. This smaller "jaw joint" is subsequently again converted into the large model corresponding to the human jaw joint, in which the movement spaces or joint spaces are delineated in the dental bite registration mold and then molded into the joint material compound in the joint registration mold according to the pantograph principle. In this way, an articulator joint corresponding to the real jaw joint, is accomplished, which can be advantageously used in order to accordingly work with such an articulator exactly as with the patient. Light-curing plastic or 2K plastic, but also kneadable 2K silicon can preferentially be used as such a material. In their position, the hemispheres lean on the so-called Bonwill's triangle. The size of this triangle should be ⅕-⅙ of the Bonwill's triangle. The dental bite registration trays or dental bite registration molds are arranged at the vertices of the triangle, the hemispheres then molding the joint spaces therein. These movements should be carried out uniformly, whereby it is practical, if the lower jaw model holder is configured so as to carry out the necessary sagittal and transverse movements by hand and/or in a motor-driven manner. The work can at the same time be performed by hand and in particular with motor-driven support, or also only in a motor-driven manner.

While the support pin is also needed during the subsequent processing of the impressions or replacement teeth, this does not apply to the dental bite registration molds with their joint spaces. It is practical for this reason, if the dental bite registration molds can be connected to the upper jaw plate independently of the support pin, or that the upper jaw model holder is configured so as to have its own support pin. The dental bite registration mold and the support pin can then be used and handled as a structural unit in the latter case, wherein the actual articulator can operate with its own support pin during the subsequent work.

As already indicated in the explanation of the method, it is possible to fit the joint space duplicates produced in the patient's mouth jointly with the dental bite registration mold and material directly in the articulator interacting with the joint balls. The transfer of the joint space molds is not necessary precisely if an articulator is used into which the joint space duplicates produced in the mouth can be inserted.

According to another embodiment, it is provided that the movement spaces replicating the individual articulator joints and thus the joint space duplicates are manufactured intraorally by means of the lower jaw movements of the patient directly or while interposing a data storage in the material of the dental bite registration mold, wherein the dental bite registration mold of the lower jaw plate and hemispheres of the lower jaw plate creating the movement spaces are allocated to the lower jaw plate, or that the movement spaces are electronically recorded and further processed electronically directly into joint space duplicates according to the data, or that the joint movement spaces are formed by being molded in elastic curable joint material. This has the great advantage that joint space duplicates can then also be directly produced, which can be mounted in the respective articulator. Reference is hereby made that mechanical material molds are not necessarily required, but that the work can also be carried out with electronic variants or similar registration methods that make possible to identically, or at least identically, shape the mold or movement spaces of the patient's jaw joint to form a joint space duplicate as an articulator joint for such articulators.

In order to improve the method and also in order to optimize the device, it is advantageous, if the articulator has a bearing ring that takes over the Camper's plane measured in the patient, which is allocated to the upper part of the articulator. This bearing ring is equipped with a support ring that can be adjusted via a telescope. Via such an auxiliary device it is possible to determine the position that is relevant to the determination and fixation of the occlusal plane, namely by determining the Camper's plane, which can then be practically adducted by means of the telescope legs operating in parallel in or on the plaster model in such a way that the dental technician or the treating professional can accurately determine the position of the occlusal plane. This is advantageously possible because the occlusal plane and the Camper's plane represent planes that are parallel to each other. In addition to the adjustment or determination of the occlusal plane, it is also important for handling an articulator to be able to adjust or set different dental occlusions. This was only necessary with great effort in the previous devices or articulators, that is, the upper jaw model had to be removed and again fixed by means of another adjustment on the upper part of the frame, so that a new articulation was necessary. This great effort is frequently not made by dental technicians, especially because of the risk that damage may occur in the process, which will require another registration of the models. By means of the invention it is, however, possible to represent different dental occlusions without a change to or adaptation of the single articulator, which is attained according to the invention in that the movable upper part of the frame is articulately connected to the bottom part of the frame via swivel joints with a swivel arch that connects them, and guided via the articulator joints, wherein the upper part of the frame can be additionally fixed on the swivel arch via an adjustable position stabilizer and allocated to the bottom part of the frame so as to spatially swivel via the articulator joints. In this context, this position stabilizer is configured in such a way that it makes possible different dental occlusions without having to modify the used upper jaw model or having to release it from and correspondingly adaptively attach it again to the upper part of the frame. Here, it is possible to specifically bring the upper part of the frame to a position that represents the new bite, which is either predetermined by the dentist or proposed by the dental technician, so that all necessary adaptations to the teeth or the bridges to be inserted are possible.

In this connection it is advantageous that a default part used for articulating the basic position in the position stabilizer in order to modify the dental occlusion can be replaced by the desired lens-shaped free form part that predetermines the new dental occlusion. This "adaptation" of the dental occlusion is thus downright simple and saves another re-articulation. The default part or standard part is rather replaced by only one specific free form part, which predetermines a new dental occlusion, so that the entire conversion of the articulator has already been completed, and the work can accordingly be performed rapidly and easily. In order to manufacture or make available the corresponding free form parts it is advantageous if the lens-shaped free form part consists of a support part, which is configured so as to make possible a fixed coupling to the upper part of the frame or to the swivel arch, and a lens part, which is made of plastic and molded by means of a predetermined approximation of the bottom part of the frame and the upper part of the frame, and is then cured. Such free form parts are created by supplementing a support part that makes possible a fixed coupling of the position required for the upper part of the frame to the fixed position of the lower part of the frame with these lens-shaped parts. This free form is produced in that freely moldable plastic is applied to the support part, which is molded/modeled via a defined approximation of the upper part and lower part (dental bite registration mold) and subsequently cured. The free form part obtained in this way makes possible a stable and reproducible positioning. In this way, it becomes possible to rapidly and easily reproduce, comparatively represent for diagnostic procedures and also rapidly and securely correct even the most subtle deviations of the patient's dental occlusion.

Besides the default part or free form part, the position stabilizer as such is provided with an axis that can be fixed by means of ball joints with torque support on the swivel arch and again released. In this way, the possibility is given to simply carry out the up and down movements of the upper part during fixation, while all spatially oriented movements of the upper jaw model can be carried out when the axis is released. In this case, it is advantageous if the default part and the lens-shaped free form parts can be arranged displaceable between the ball joints and the axis.

In the known articulators, so-called support pins are used in order to hold the upper part of the frame in a predetermined position. The tip of the support pins is guided in a kind of plate in order to predetermine or easily reach the respectively optimal position in this way. It is disadvantageous that this support pin actually always represents an obstacle, if the dental technician wants to handle or also move the upper or lower jaw model. This problem is eliminated according to the invention in that the support pin, which is required for the fixation of a vertical upper-lower jaw position and is configured as a fixing pin, is arranged in the retral space of the articulator and is fixed on the stationary bottom part of the articulator frame so as to interact with a dental bite registration tray receiving a curable pin material and is allocated to the upper part of the frame. This dental bite registration tray with the curable pin material takes over the task of the plate in the conventional support pin, so that the necessary position can always be easily reached with the vertical movement. As the support pin or fixing pin is now positioned in the rear area of an articulator, the front area with the upper and lower jaw models is easy to reach and see which precisely had previously been more difficult because of the upstream support pin. According to a practical further development it is provided that the fixing pin is mounted behind the articulator joints in the retral space of the articulator and arranged on the lifted curved part of the bottom part of the frame, while the dental bite registration tray is allocated to the movable upper frame part. This makes possible an arrangement of the fixing pin with accessories, which is as advantageous as possible and requires as little space as possible.

The invention is especially characterized in that a method and a device are created, with which it is possible to transfer the human jaw joints in such a way to the device, that is, to the articulator, that the correct movements of the patient can be performed with this articulator, which are required by the dental technician in order to mold or restore the dental prostheses or the complete denture in such a way that the dentist can insert them in the patient, possibly without any finishing, and then completely fulfill their function. This is possible because according to this method the jaw joints, which are not visible per se, can be transferred with their movement spaces or joint spaces between the fossa and condyles to an intermediate carrier or a joint space duplicate. They are then inserted into the articulator in order to accurately carry out the described movements as they are performed by the patient in the original when he accordingly moves his lower jaw, or his lower jaw is moved by the treating dentist. In this context, it is also possible to exactly adjust the occlusion plane as it is in the patient, namely with any articulator, so that also the necessary subtleties can be taken into consideration in order to create the original replacement teeth. It is furthermore advantageous that the area with the upper and lower jaw models is well visible and made accessible by the displacement of the previous support pin to the retral space of the articulator, wherein the support pin, which was previously affixed in the front, is now configured as a fixing pin affixed in the rear, allowing an accurate arrangement at all times because the fixing pin is positioned in the moldable and curable material. An enormous advantage is finally connected to the fact that the upper part of the frame with the upper jaw model is connected to the bottom part of the frame via articulator joints, which are configured in accordance with the original jaw joint and are held via an adjustable position stabilizer in such a way that even many different dental occlusions can be adjusted without the need for removing, re-articulating or even re-configuring the upper jaw model in general. The position stabilizer not only makes possible two, but also several different dental occlusions without requiring a great effort.

Further details and advantages of the subject matter of the invention are disclosed in the following description of the corresponding drawings, in which a preferred exemplary embodiment with the necessary details and individual parts is represented. The drawings show:

DETAILED DESCRIPTION

Figure 1:
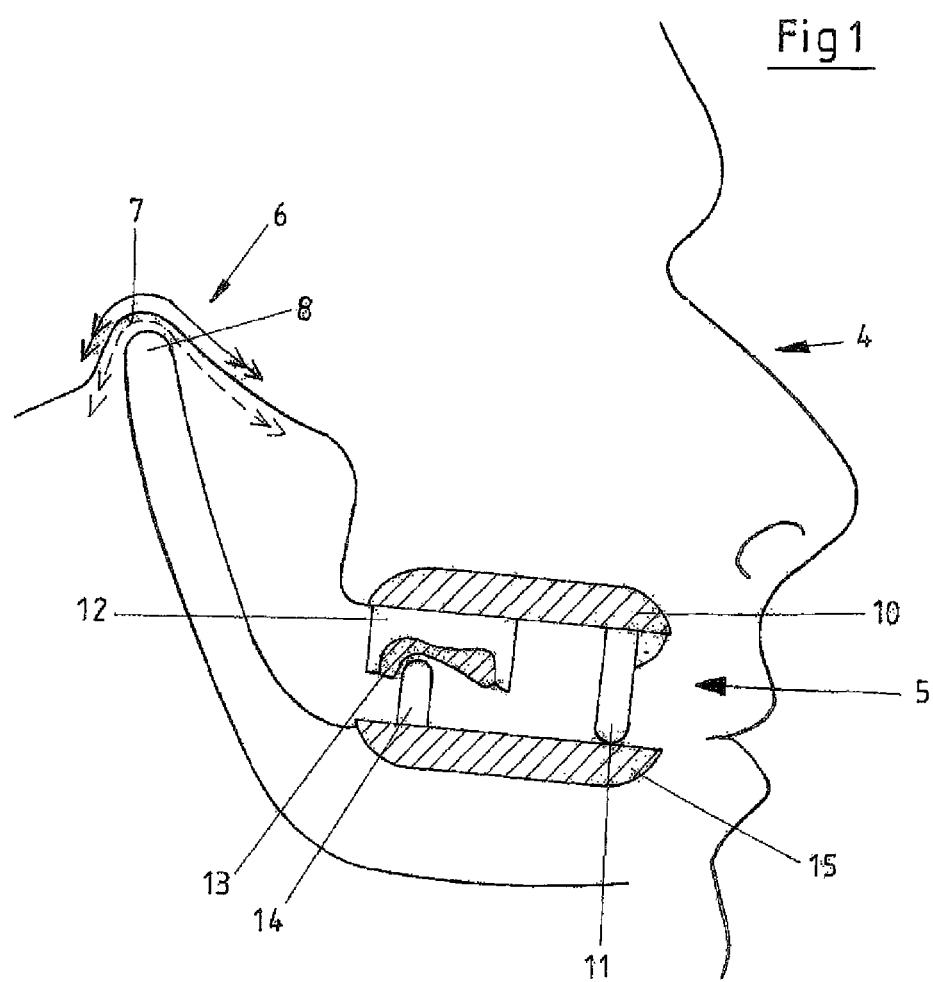
FIG. 1 a schematically depicted jaw joint situation with inserted pre-device, FIG. 2 an articulator with a dental bite registration mold and molded compound for the transfer of the joint space duplicate, FIG. 3 an articulator with an articulator joint using a joint space duplicate, FIG. 4 an articulator indicating the Camper's plane and occlusion plane, FIG. 5 an articulator with the support ring that predetermines the occlusion plane and the bearing ring that represents the Camper's plane, FIG. 6 an articulator with position stabilizer and a fixing pin in the retral area, FIG. 7 a default part of a position stabilizer, FIG. 8 different embodiments of a free form part of a position stabilizer, FIG. 9 a ball joint with torque support of the position stabilizer, FIG. 10 a lateral view of the position stabilizer with its individual parts, FIG. 11 a front view of an articulator according to FIG. 6, and FIG. 12 a perspective view of the articulator according to FIG. 6.

FIG. 1 shows a lateral view of the head of a patient 4, wherein one of its jaw joints 6 with the fossa 7 and the condyles 8 is schematically indicated. The so-called pre-device 5 consisting of the upper jaw plate 10 and the lower jaw plate 15 is arranged in the patient's mouth. The lower jaw plate 15 is equipped with one or several measuring sensors 14, while the upper jaw plate 10 has the support pin 11 known per se, as well as the dental bite registration mold 12. Plastic material 13 is filled into this dental bite registration mold 12 and is molded during the movement of the jaw joint 6 or the lower jaw of the patient 4 by means of the measuring sensors 14 according to the position of the jaw joint 6 or the movement spaces existing there. The movement space or the joint space of the natural jaw joint 6, which is predetermined by the fossa 7 and the condyles 8, thus corresponds to the movement space 22 or the joint space created in the plastic material 13.

Figure 2:
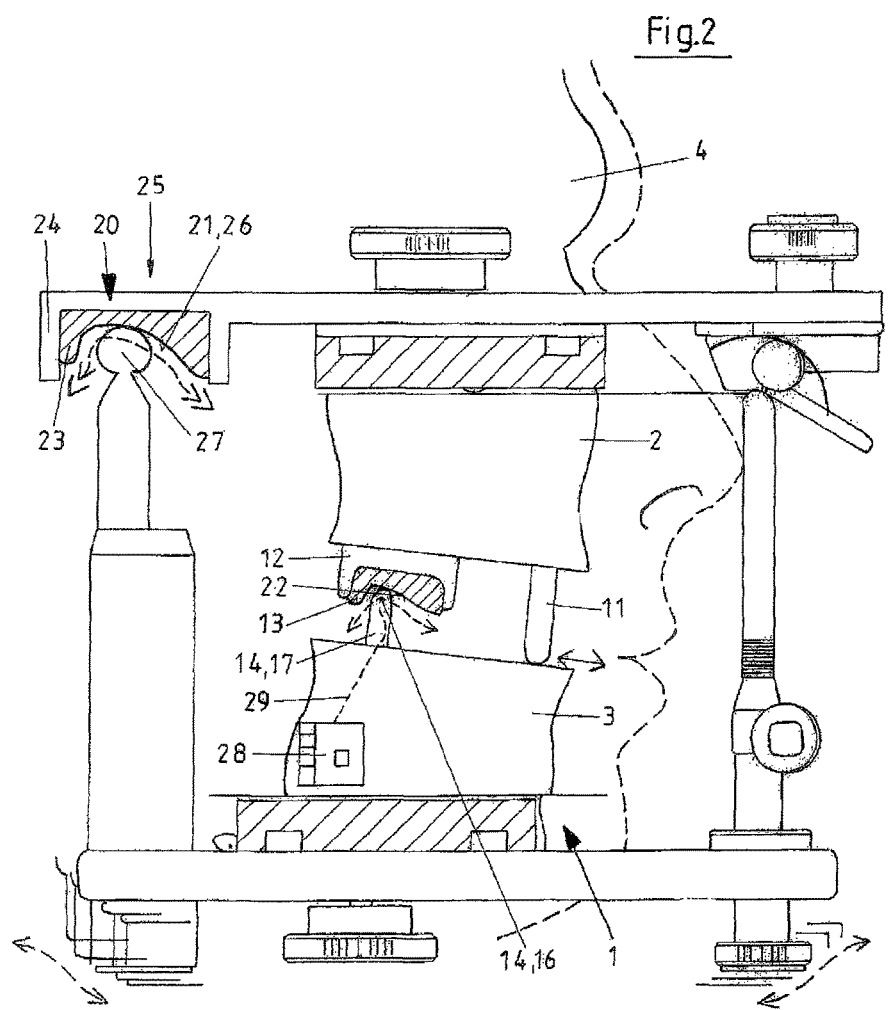

FIG. 2 initially depicts an articulator 1. Such articulators 1 are used for the mechanical simulation of movements of the lower jaw with respect to the upper jaw in fixed models, that is, the upper jaw model holder 2 and the lower jaw model holder 3. It is essentially used for two tasks, namely the diagnosis of the position and movement of the mutually opposite dental arches, on the one hand, as well as for the manufacture restorations from inlays to dental prostheses in a laboratory, on the other hand. In both cases the objective is a transfer of the mouth situation to the articulator that is as naturally as possible in order to detect occlusion problems and facilitate a trouble-free occlusion to the patient, also after inserting the new teeth or bridges.

In the articulator 1 represented in FIG. 2, the lower jaw model holder 3 is equipped with measuring sensors 14 in the form of transfer pins 17 with hemispheres 16 fitted on top thereof. The upper jaw model holder 2 again has the support pin 11, which is either allocated thereto, or represents a structural unit together with the dental bite registration mold 12, wherein this dental bite registration mold 12 already has the molded and cured plastic material 13. As the lower jaw, or, more precisely, the upper jaw, is moved by the articulator 1, the hemispheres 16 delineate the movement spaces 22, or the joint spaces in the plastic material 13. In this embodiment, the otherwise customary articulator joint 20 is equipped with joint material 23 by means of a joint registration mold 24, wherein the joint material 23 is practically identical with the plastic material 13. According to the pantograph principle, one joint movement space 26 or several joint spaces are now molded in the joint material 23 during the movement of the lower jaw and the delineation of the movement spaces 22. The hemisphere 27 is part of the articulator 1, which forms the corresponding joint movement spaces 26 or the joint space duplicates 21. A joint space duplicate 21 corresponding to the natural jaw joint 6 of the patient 4, which now can be or is used with the hemisphere 27 as articulator joint 20 at the swivel joint position 25 is created in this way with the pantograph principle.

Besides the described transfer of the movements according to the pantograph principle or production of the corresponding joint space duplicates in the area of the articulator joint 20 the possibility is also given that the movements performed by the measuring sensor 14 within the movement spaces 22 are determined, implemented and stored by means of the measuring sensor 14 and a built-in data storage 28 in order to be used later, or whenever necessary, for the production of the patient's correct joint space duplicate 21. The connecting line to the measuring sensor 14 is identified with reference numeral 29, wherein also other connection possibilities are conceivable.

Since the created joint movement spaces 26 are a three-dimensional reproduction of the movement spaces 22, or of the joint space duplicates 21, or of the natural jaw joints 6, all of the possible movements of the lower jaw can be carried out after correspondingly modifying or equipping the articulator 1, namely according to the exact data of the patient in the sagittal as well as in the transverse direction.

Figure 3:
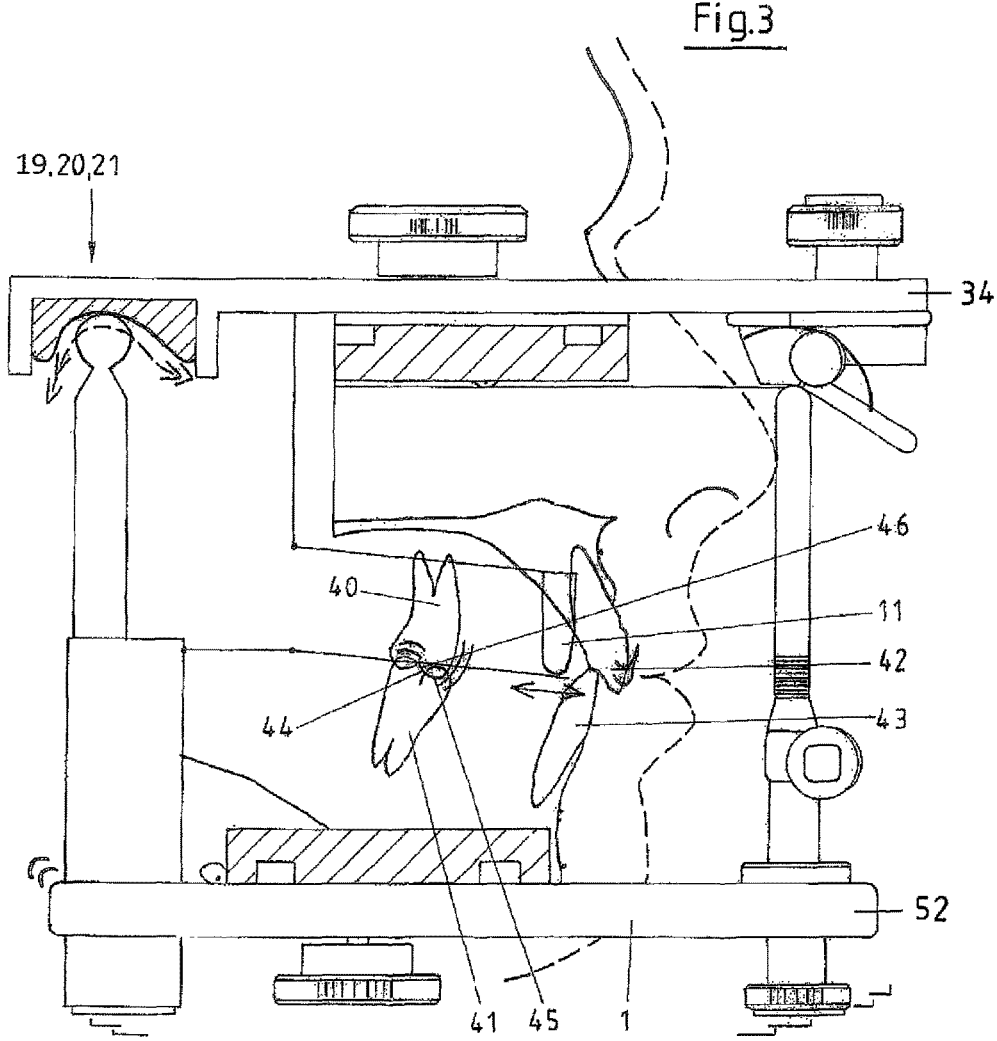

FIG. 3 shows the articulator being used in a dental technology laboratory, wherein a corresponding dental prosthesis of any kind can now be produced in the articulator 1 "programmed" in this way. It is only necessary for this purpose to remove the dental bite registration mold 12 with the plastic material 13 and the measuring sensors 14 from the system, while the support pin 11—regardless of the type—remains in place because it is required for the further work of the mutually correlating system of support pins—synthetic jaw joint or joint space duplicates 21. The corresponding joint space duplicate 21, which in fact functions as an articulator joint 20 together with the hemispheres 27, as well as the support pin 11 and a tooth 40 in the upper jaw and a tooth 41 in the lower jaw can be seen in FIG. 3, wherein it is indicated that the latter are arranged in such a way that the contact points 44 are optimally positioned and the humps 45 and pits 46 correctly rub against each other and are guided. Reference numerals 42 and 43 identify the incisors of the upper jaw and lower jaw.

Figure 4:
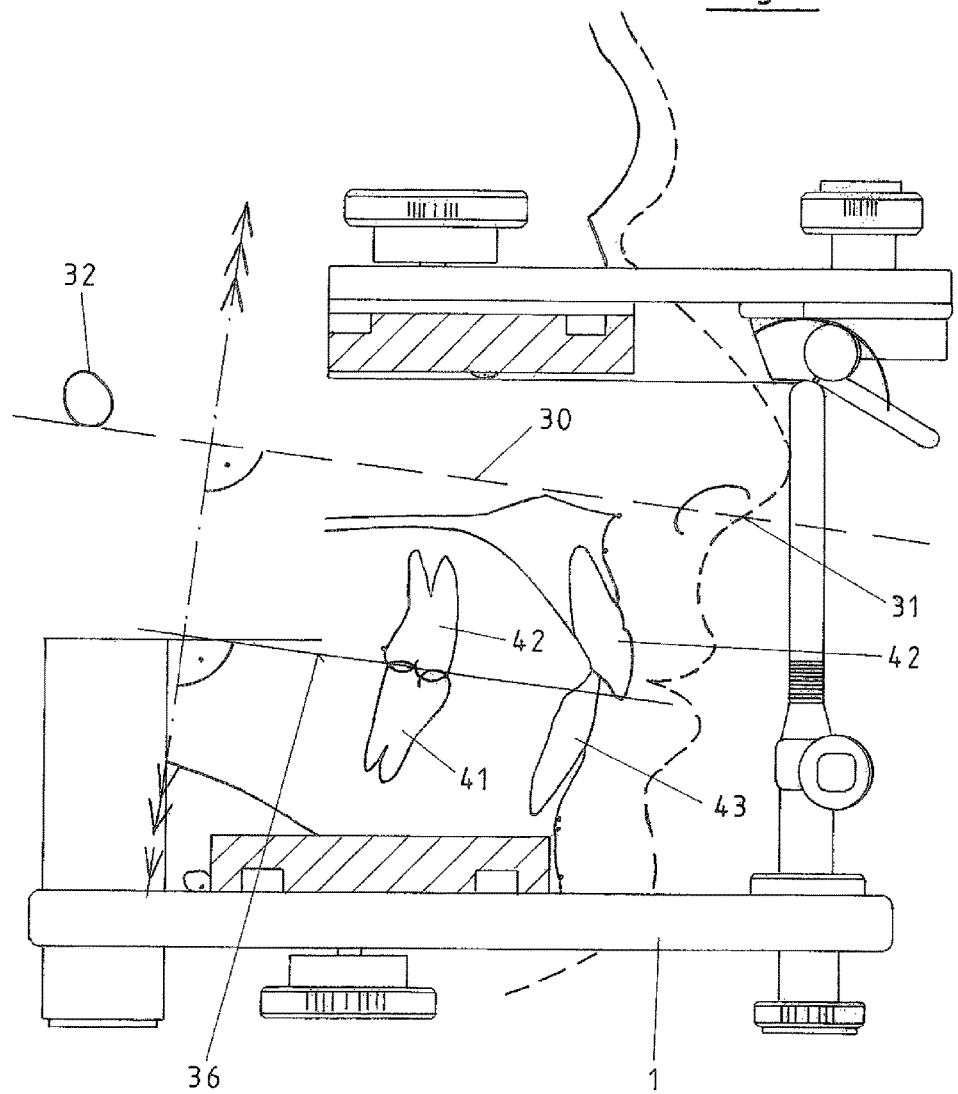
Figure 5:
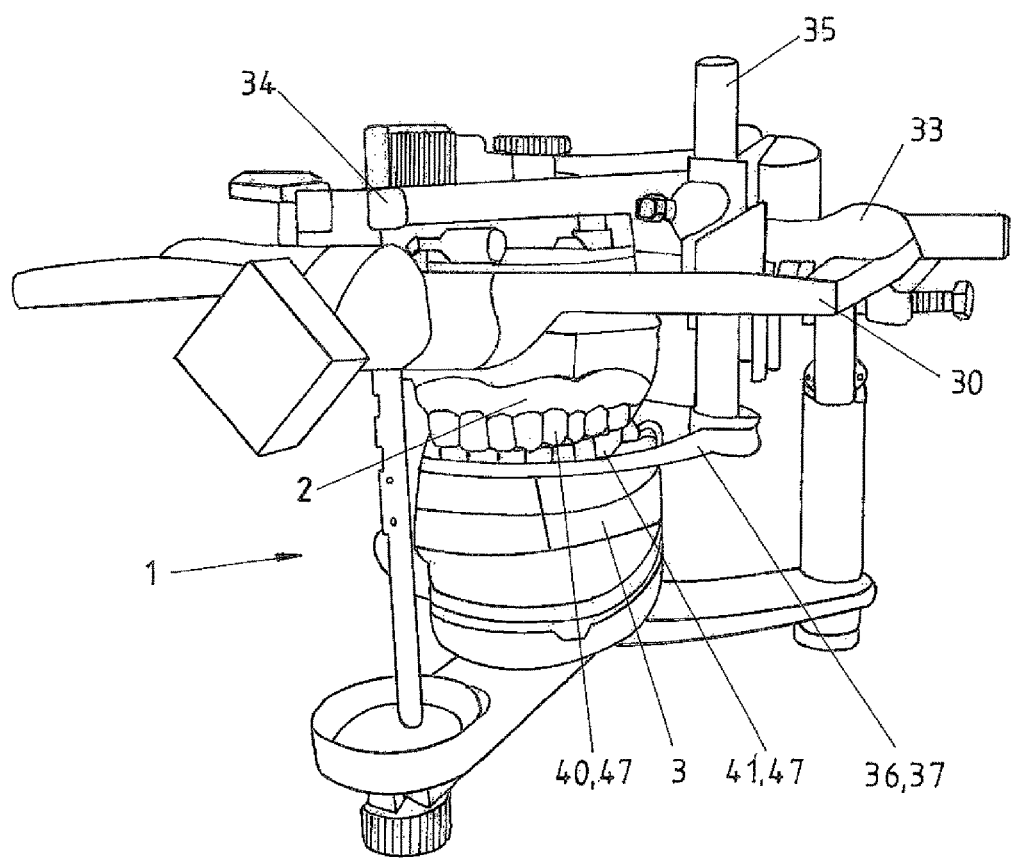

FIG. 4 shows a largely similar drawing, with the exception that besides the said teeth 40, 41, 42, 43, the occlusal plane 36 and the Camper's plane 30 are also indicated. The Camper's plane 30 to be determined on the patient 4 runs between the nose 31 and the ear 32 of the patient 4. It is represented in FIG. 5 by the bearing ring 33, which is held on the upper part 34. Via telescoping legs 35, the support ring 37 with the occlusal plane 36 has been exactly placed in the position, which the dental technician needs this occlusal plane 36 for a correct observation of the upper and lower jaw movements in the articulator 1. Reference numeral 47 additionally identifies the patient's model teeth included herein. It can be seen that the correct position of the occlusal plane 36 can be securely and rapidly adjusted with such a device or mechanism. Another parameter, which is necessary for a restoration according to the latest scientific findings, can be included in this way in the reconstruction of the dental prosthesis.

FIG. 6 shows a particularly user-friendly articulator 1, which consists of the upper frame part 34, which can be held swivelable on an elegantly configured bottom frame part 52. The actual bottom frame part 52 with the lower jaw model, which is not depicted here, is provided with an especially shaped articulator frame 53, wherein the bottom frame part 52 is connected to the upper frame part 34 via an S-like curved part 57.

It can be seen that the front part of the articulator 1, where the jaw models are mounted, can be totally freely accessed because the support 11 configured as a fixing pin 50 is allocated here to the retral space 51 of the articulator 1. For this purpose, the curved part 57 is guided upward via the upper frame part 34 and provided with a holder for the fixing pin 5. A dental bite registration tray 56 with pin material 55 is allocated to the end of the upper frame part 34 located underneath it, wherein this pin material 55 is curable, so that the correct position and arrangement of the fixing pin 50 can thus be consistently predetermined in the dental bite registration tray 56.

The actual upper frame part 34 is connected to the bottom frame part 52 via a swivel arch 60 and via the articulator joints 20 and 61. The swivel arch 60 can be swivelably articulated via swivel joints 58, 59 on the bottom frame part 52 or on the swivel arch 57.

Besides the retral arrangement of the fixing pin 50, it can also be seen that the upper frame part 34 is provided in the upstream area with a beak tip 80, which makes it easier to carry out the necessary movements with the upper frame part 34 in order to be able to also imitate the movements carried out by the jaw of the respective patient 4.

Figure 12:
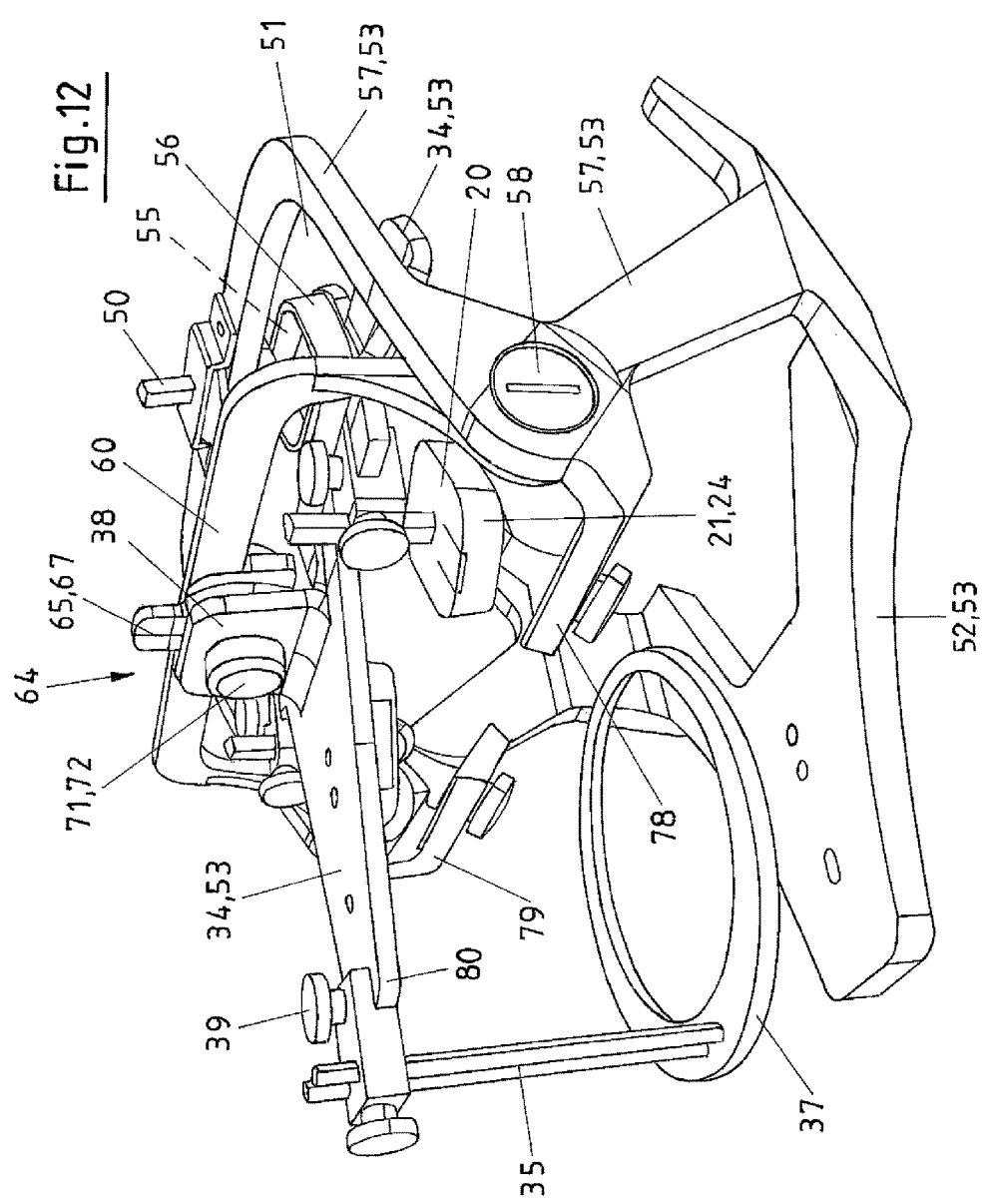

As shown in FIG. 12, the optimization of these movement possibilities can be seen in that the upper frame part 34 and a position stabilizer 64 can be fixed on the swivel arch 60 via an attachment 38. FIG. 6 indicates that this position stabilizer consists of an axis 75, which can be fixed on and again released from the swivel arch 60 at one end via a ball joint 71 with sleeve 72 and torque support 74 and on the other end via a ball joint 73. A default part 65 with a handle piece 67 is interposed, which is easy to remove and can be replaced, as indicated in FIGS. 7 and 8, by means of a similarly designed free form part 66. This free form part 66 consists of a support part 68 and the lens parts 69, 70 arranged on both sides, which are made from curable plastic and predetermine the respective dental occlusion. The free form parts 66, 66', 66" are accordingly shown in FIG. 8. The free form part 66 or also the default part 65 can be pushed onto the axis 75 because they are provided with an axial slot 76 having a long guide slot 81. Guide holes or fixing holes that make possible a correct positioning of the free form part 66 or of the default part 65 on the axis 75 are identified with reference numeral 77.

FIGS. 9 and 10 show an enlarged view of a position stabilizer 64 with the ball joint 73, which is configured in such a way that the entire position stabilizer 64 can be fixed. The swivel arch is then identified with reference numeral 60 and the free form part is identified with reference numeral 66. The attachment 38 of the upper frame part 34 as well as the ball joint 71 with the sleeve 72 and torque support 74 is subsequently shown. The latter is shown enlarged in FIG. 9.

FIG. 11 shows a front view of a corresponding articulator 1 according to FIG. 6, wherein it can be seen that the upper frame part 34 is connected to a swivel arch 60 and can carry out movements that are guided by means of articulator joints 20 and 61 with the joint space duplicates 21 accommodated therein. These articulator joints 20, 61 interact with the joint balls 19, 62, which are held via holders 63, 63' on corresponding bow mounts 78, 79 of the bottom frame part 52. These joints 20, 61 consequently make possible a movement of the upper frame part 34 with a corresponding release of the position stabilizer 64 precisely in the way predetermined by the natural jaw joint 6 of the patient 4. It can also be seen that the front area with the upper and lower jaw models can be easily reached and basically easily seen because the fixing pin 50 is accommodated in the retral space 51. This can also be seen in FIG. 12, wherein, however, a support ring 37 with telescopic leg 35 and fixing part 39 is allocated to the beak tip 80 of the upper frame part 34 in order to regulate the occlusal plane. After the adjustment of the occlusal plane, this component can again be removed, so that the area in the front between the front-mounted parts of the upper frame part 34 and the bottom frame part 52 can be easily reached and seen.

All the features referred to, and also those that are only apparent from the drawings, are essential to the invention, whether alone or in combination.

The invention claimed is:

1. A method for producing a dental prosthesis, in which first an impression of an upper jaw and of a lower jaw with teeth is made, and a device designated as an articulator for simulating jaw movements on dental bite registration molds, which register the corresponding upper and lower jaw impressions, is then taken to a dental technician, whereupon the dental prosthesis is molded by moving either the lower jaw impression or the upper jaw impression around articulator joints that are similar to the patient's jaw joints and are produced taking into account the lower jaw impression, then returned to the dentist, inserted in the patient, and finished by the dentist, wherein before or after the impressions of the upper and lower jaw are produced, the movement paths in the basic directions of the patient's jaw joints when the lower jaw is moved are determined, registered and used as articulator joints on the articulator for the production representation of the joint space duplicates of the patient's jaw joints, and in that this articulator equipped with articulator joints corresponding to the patient's jaw joints is then used by the dental technician to restore the dental prosthesis, wherein the movements performed by the patient's lower jaw are guided by a support pin, which is firmly held in the upper jaw via an upper jaw plate, and transferred via hemispheres allocated to a lower jaw plate, which are arranged spaced apart from each other and forming a triangle with the support pin in the support pin/jaw joint axis, while decoupling the patient's prosthesis, as a joint space duplicate in a plastic material embedded in dental bite registration mold allocated to the upper jaw plate, and further joint space duplicates of each jaw joint are manufactured using these joint space duplicates extraorally according to the pantograph principle, and used as an articulator joint in the articulator.

2. The method according to claim 1, wherein the joint space duplicates are mounted directly in the articulator, where they form the articulator joints.

3. A method according to claim 1, wherein the correct occlusion plane is adjusted on the articulator based on the Camper's plane measured on the patient during the manufacture of the dental prosthesis, with the articulator having the joint space duplicates still before or during the manufacture of the dental prosthesis.

4. A method according to claim 1, wherein on manufacturing of a corresponding dental prosthesis in the articulator is according to the method, the support pin with the upper jaw plate is still fixed in the articulator, while the joint and the joint space duplicates are removed therefrom when the dental prosthesis is manufactured and tested in the articulator.

5. A method according to claim 1, wherein the movements of the jaw joints are three-dimensionally transferred to the plastic curable material in the dental bite registration mold resulting in the intraoral joint space duplicates.

6. A method for producing a dental prosthesis, in which first an impression of an upper jaw and of a lower jaw with teeth is made, and a device designated as an articulator for simulating jaw movements on dental bite registration molds, which register the corresponding upper and lower jaw impressions, is then taken to a dental technician, whereupon the dental prosthesis is molded by moving either the lower jaw impression or the upper jaw impression around articulator joints that are similar to the patient's jaw joints and are produced taking into account the lower jaw impression, then returned to the dentist, inserted in the patient, and finished by the dentist, wherein before or after the impressions of the upper and lower jaw are produced, the movement paths in the basic directions of the patient's jaw joints when the lower jaw is moved are determined, registered and used to form articulator joints on the articulator for the production representation of the joint space duplicates of the patient's jaw joints, and in that this articulator equipped with articulator joints corresponding to the patient's jaw joints is then used by the dental technician to restore the dental prosthesis, wherein the values obtained during the articulation, when jaw joint fossa is delineated, are additionally or only electronically registered, stored and used via CadCam to form joint movement spaces in the template in a dental bite registration mold or directly for joint space duplicates.

7. The method according to claim 6, wherein different dental occlusions are rapidly and securely reproduced, comparatively presented for diagnostic procedures, and, if required, corrected in an occlusion system with the articulator having the joint space duplicates via a correspondingly adjustable position stabilizer during manufacture of the dental prosthesis, while retaining the fixation of the upper jaw model on an upper frame part of the articulator.

8. A device for simulating lower jaw movements and thus carrying out the method according to claim 1, comprising an articulator with upper jaw model holder with support pin and a lower jaw model holder, wherein the upper jaw model holder and lower jaw model holder are mutually articulately connected by articulator joints, which match human jaw joints as closely as possible, wherein the articulator is configured so that it can be connected to a pre-device with upper jaw plate and support pin, as well as dental bite registration molds and a lower jaw plate with allocated measuring sensor, with which joint space duplicates corresponding to a human jaw fossa of a patient are molded in curable plastic material of the dental bite registration molds in the mouth of the patient, which are configured and arranged in such a way that the trajectories of joint space duplicates can be transferred to curable joint material in joint registration molds of the articulator joints according to the pantograph principle.

9. The device according to claim 8, wherein the articulator joints or the joint space duplicates that reproduce the human jaw joint fossa are configured releasable and replaceable by the joint space duplicates of the respective patient.

10. The device according to claim 8, wherein the pre-device has a releasable upper jaw plate with support pin and a releasable lower jaw plate with transfer pins configured as hemispheres as measuring sensors, which are arranged therewith so as to form a triangle in a support pin/jaw joint axis, that the upper jaw plate is equipped with the dental bite registration molds filled with the plastic curable material in addition to the support pin, which are positioned in correspondence with the hemispheres of the measuring sensor, and that the articulator joints of the articulator are formed by the joint space duplicates of the respective patient with joint balls of the articulator joints, which are produced extraorally corresponding to the jaw joints of the patient by scanning movement space fossa in the dental bite registration molds according to the pantograph principle in the plastic curable joint material in the joint registration molds, and which are arranged at a swivel joint site of the articulator.

11. The device according to claim 10, wherein the joint space duplicates produced in the mouth of the patient with the dental bite registration molds and the material are directly inserted into the articulator interacting with the joint balls.

12. The device according to claim 8, wherein a support pin for the determination of a vertical upper-lower jaw position configured as a fixing pin is arranged in a retral space of the articulator and is fixed on a stationary bottom frame part of an articulator frame interacting with a dental bite registration tray that receives a curable pin material and is allocated to an upper frame part.

13. The device according to claim 12, wherein the fixing pin is mounted behind the articulator joints in the retral space of the articulator and arranged on a lifted curved part of the bottom frame part, while the dental bite registration tray is allocated to the movable upper frame part.

14. The device according to claim 12, wherein a movable upper frame part is articulately connected to the bottom frame part via swivel joints with a swivel arch and guided via the articulator joints, wherein the upper frame part can be additionally fixed in the swivel arch via an adjustable position stabilizer and is allocated to the bottom frame part so as to spatially swivel via the articulator joints.

15. The device according to claim 14, wherein a default part used for the articulation of the basic position in the position stabilizer in order to modify the dental occlusion can be replaced by a desired lens-shaped free form part that predetermines the new dental occlusion.

16. The device according to claim 15, wherein the lens-shaped free form part comprises a support part, which is configured so as to make possible a fixed coupling to the upper frame part or to the swivel arch, and a lens part, which is made of plastic and molded by a predetermined approximation of the bottom frame part and the upper frame part and subsequently cured.

17. The device according to claim 15, wherein the position stabilizer is configured connecting the upper frame part and the swivel arch via an axis that can be fixed and again released by means of ball joints with torque support.

18. The device according to claim 17, wherein the default part and the lens-shaped free form parts are arranged between the ball joints and displaceable on the axis.

19. A method for producing a dental prosthesis, in which first an impression of an upper jaw and of a lower jaw with teeth is made, and a device designated as an articulator for simulating jaw movements on dental bite registration molds, which register the corresponding upper and lower jaw impressions, is then taken to a dental technician, whereupon the dental prosthesis is molded by moving either the lower jaw impression or the upper jaw impression around articulator joints that are similar to the patient's jaw joints and are produced taking into account the lower jaw impression, then returned to the dentist, inserted in the patient, and finished by the dentist, wherein before or after the impressions of the upper and lower jaw are produced, the movement paths in the basic directions of the patient's jaw joints when the lower jaw is moved are determined, registered and used as articulator joints on the articulator for the production representation of the joint space duplicates of the patient's jaw joints, and in that this articulator equipped with articulator joints corresponding to the patient's jaw joints is then used by the dental technician to restore the dental prosthesis, wherein movement spaces that replicate individual articulator joints and thus the joint space duplicates are manufactured intraorally by means of lower jaw movements of the patient directly or while interposing a data storage in material of the dental bite registration molds, wherein a dental bite registration mold of the upper jaw plate and hemispheres of a lower jaw plate, which transfer the movement of the lower jaw of the patient and create the movement spaces, are allocated to the lower jaw plate, or that the movement spaces are electronically recorded and electronically further processed directly to the joint space duplicates according to the data, or the joint movement spaces are formed by molding in elastic curable joint material.

20. A method for producing a dental prosthesis, in which first an impression of an upper jaw and of a lower jaw with teeth is made, and a device designated as an articulator for simulating jaw movements on dental bite registration molds, which register the corresponding upper and lower jaw impressions, is then taken to a dental technician, whereupon the dental prosthesis is molded by moving either the lower jaw impression or the upper jaw impression around articulator joints that are similar to a patient's jaw joints and are produced taking into account the lower jaw impression, then returned to the dentist, inserted in the patient, and finished by the dentist, wherein before or after the impressions of the upper and lower jaw are produced, the movement paths in the basic directions of the patient's jaw joints when the lower jaw is moved are determined, registered and used as articulator joints on the articulator for the production representation of the joint space duplicates of the patient's jaw joints, and in that this articulator equipped with articulator joints corresponding to the patient's jaw joints is then used by the dental technician to restore the dental prosthesis, wherein an articulator has a bearing ring that takes over a Camper's plane measured on the patient, which is allocated to an upper part of the articulator.

* * * * *